United States Patent [19]

Zhu

[11] Patent Number: 5,734,084
[45] Date of Patent: Mar. 31, 1998

[54] SYNTHESIS OF ALKYLATED AROMATIC AMINES

[75] Inventor: Ping Y. Zhu, Willoughby Hills, Ohio

[73] Assignee: The Lubrizol Corporation, Wickliffe, Ohio

[21] Appl. No.: 767,765

[22] Filed: Dec. 17, 1996

[51] Int. Cl.⁶ .................................................. C07C 209/68
[52] U.S. Cl. ............................................................ 564/409
[58] Field of Search .............................................. 564/409

[56] References Cited

U.S. PATENT DOCUMENTS

| | | | |
|---|---|---|---|
| 2,558,285 | 6/1951 | Wilson et al. | 260/576 |
| 3,275,690 | 9/1966 | Stroh et al. | 260/576 |
| 3,368,975 | 2/1968 | Davis et al. | 252/51.5 |
| 3,505,225 | 4/1970 | Wheeler | 252/33.6 |
| 3,601,632 | 8/1971 | Frazier | 307/219 |
| 4,351,958 | 9/1982 | Takahata et al. | 564/409 |
| 4,605,766 | 8/1986 | Hargis | 564/409 |
| 4,770,802 | 9/1988 | Ishida et al. | 252/50 |
| 4,824,601 | 4/1989 | Franklin | 252/401 |
| 4,846,985 | 7/1989 | Abbas et al. | 252/47.5 |
| 5,520,848 | 5/1996 | Evans | 252/405 |
| 5,607,890 | 3/1997 | Chen et al. | 502/202 |

*Primary Examiner*—Brian M. Burn

[57] ABSTRACT

An improved method for making alkylated aromatic amines is disclosed. The method includes a new alkylating catalyst system comprising an aromatic amine alkylating catalyst and a non-catalyst solid such as silica. The method results in faster reaction rates and higher yields of alkylated aromatic amines.

14 Claims, 2 Drawing Sheets

SYNTHESIS OF ALKYLATED AROMATIC AMINES

BACKGROUND OF THE INVENTION

Aromatic amine alkylation with an alkylating agent and Friedel-Crafts, acidified clays (silica-aluminas) and Lewis acid catalysts are well-known reactions. For example, see U.S. Pat. Nos. 2,558,285; 3,601,632; 3,368,975; 3,505,225; and 4,846,985 which are incorporated herein by reference for disclosure of alkylated aromatic amines and their mode of synthesis.

U.S. Pat. No. 4,824,601 describes the synthesis of 4,4'-dioctyldiphenylamine from diphenylamine and diisobutylene in less than 25% by weight based on the yield of reaction products using activated earth catalyst, Fulcat® 22B, and a molar ratio of up to 2.5:1 for the diisobutylene to amine. The residual diphenylamine was below 10% by weight of the reaction products.

U.S. Pat. No. 4,770,802 describes alkylating phenyl-alphanapthylamine with aluminum chloride, activated clay, or a combination of the two alkylating catalysts. The amine was mono-alkylated in high yield on the para-position of the phenyl ring.

U.S. Pat. No. 3,275,690 describes the mono and dialkylation of aniline by isobutene using aluminum chloride and other Friedel-Crafts' catalysts. The '690 patent also discloses the use of bleaching earths and bleaching earths in combination with Friedel-Crafts' catalysts to alkylate aromatic amines with olefins. Catalysts claimed were aluminum chloride, aluminum bromide, iron chloride, boron fluoride, zinc chloride, tin tetrachloride, vanadium trichloride, silicon-tetrachloride and titanium tetrachloride. In addition, Friedel-Crafts' catalysts in combination with materials containing aluminum, lithium, sodium, potassium, rubidium, cesium, barium, calcium, strontium and magnesium were also claimed.

U.S. Pat. No. 5,520,848 discloses alkylating diphenylamines with diisobutylenes using activated alumina catalyst (Fulcat® 22B)

SUMMARY OF THE INVENTION

We have found that when catalyst systems comprising aluminum chloride or other Lewis acid Friedel-Crafts, Super Lewis acids or Bronsted Lewis acids or mixtures thereof in the presence of a non-catalyst solid are used to alkylate aromatic amines, increased rates of alkylation are obtained and amounts of aromatic amine starting compounds remaining in the reaction mixture are reduced. The primary reaction products are mono and dialkylated aromatic amines. We have also found that by use of this alkylating system the yield of dialkylated aromatic amines increases.

Benefits caused by improvements to an alkylating system for aromatic amines using the alkylating catalyst/non-catalyst solid are apparent. Because of the increased reaction rates, more product can be made using the same equipment per unit time. Also, less alkylating agent can be used with a constant amount of aromatic amine since the alkylation reaction using the alkylating catalyst/non-catalyst solid is more efficient. Further, the amount of starting aromatic amine remaining in the reaction products is lower due to increased alkylation reactivity when the catalyst system of this invention is employed.

A BRIEF DESCRIPTION OF THE DRAWINGS

FIG. 1. Alkylation of Diphenyl Amine
FIG. 2. Disappearance of Diphenyl Amine

DETAILED DESCRIPTION OF THE INVENTION

Figure 1:
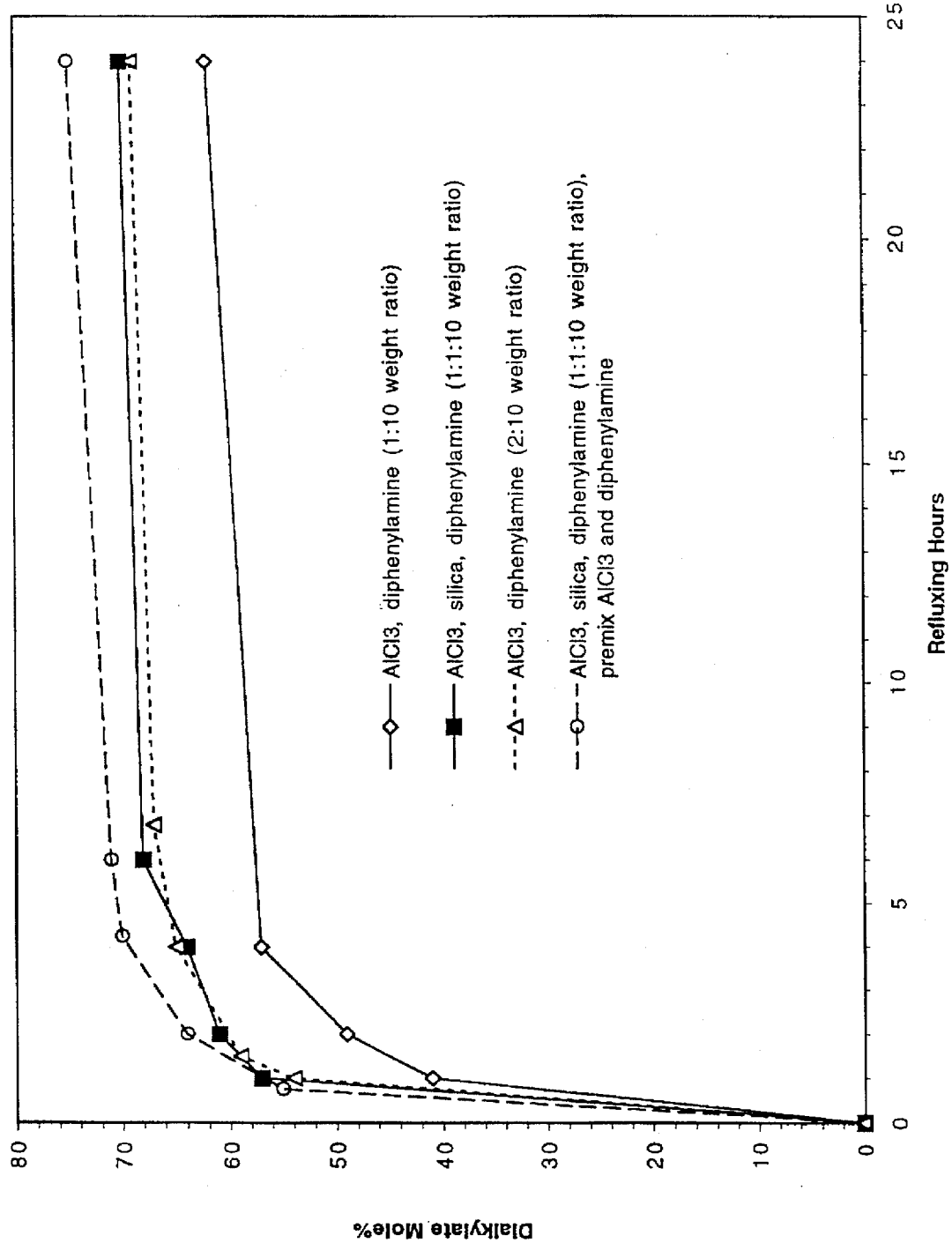

The references cited above give detailed instructions for the synthesis of alkylated aromatic amines using Lewis acid/Friedel-Crafts/activated earths catalysts and mixtures thereof. In the examples below we give details of the synthesis of alkylated aromatic amines by the methods of this invention and comparative synthesis by standard procedures.

EXAMPLE 1

Alkylation of Diphenylamine 25.4 grams (0.15 mole) diphenylamine and 2.54 grams anhydrous aluminum chloride were mixed and heated to 150° C. and 51.1 grams (0.405 mole) nonene added over 20 minutes. The mixture was refluxed for 24 hours. The reaction mixture was cooled, quenched with water and extracted with aqueous alkali solution followed by water. The organic layer was filtered through filter aid and the unreacted nonene evaporated under vacuum leaving a residue of 42 grams of product plus starting material.

EXAMPLE 2

Improved Alkylation of Diphenylamine

The alkylating procedure of Example 1 was followed with the exception that an equal weight of silica was added with the aluminum chloride. The procedure was otherwise the same.

The products of the reactions in Examples 1 and 2 were measured by NMR analysis. Aliquots were taken from the reactions at various times and amounts of dialkylated diphenylamine and residual diphenylamine were determined.
Nuclear Magnetic Resonance Analysis of Diphenylamine Alkylation Reaction In the $^1$H-NMR method, chemical shifts are assigned to NH peaks in various environments and from these peak areas yields of dialkylates can be calculated. NMR spectrum have been recorded in $CDCl_3$ with a FTNMR instrument. NMR peak assignments are as listed below:

| N$\underline{H}$ from diphenylamine | 5.6 ppm |
| N$\underline{H}$ from para-monoalkylate | 5.53 ppm |
| N$\underline{H}$ from para-dialkylate | 5.47 ppm |

The yields of mono and dialkylates and residual diphenylamine can be calculated by the areas under the respective peaks using deconvolution methods.

Examples 1 and 2 above give specific reaction parameters for reacting diphenylamine with nonene. It should be recognized that other reaction parameters are also useful depending upon the reactants, the amounts of catalysts and so on as would be easily recognized by one skilled in the art. Aluminum chloride and various silicas were used for the inventive catalyst species.

For comparative purposes, nonene was used to alkylate diphenyl amine with the mole ratios of nonene to diphenylamine varying from 1:1 to 3.5:1. For alkylations using aluminum chloride alone, the weight ratio of diphenylamine to aluminum chloride was 10:1, but weight ranges varying from 10:0.1 to 10:3 were also used.

When aluminum chloride was used in mixture with a non-catalyst solid, the same weight ranges of aluminum chloride to diphenylamine as stated above were also used. The non-catalyst solid used together with aluminum chloride has weight ratios of aluminum chloride to solid of 10:1 to 1:10, with a preferred range being 2:1 to 1:2, with a more preferred range being 1:1 for aluminum chloride to non-catalyst solid. Thus in a preferred mode, the diphenylamine alkylation of this invention had weight ratios of 10:1:1 for diphenylamine, aluminum chloride, and non-catalyst solid.

A non-catalyst solid as used in this invention is defined as a solid, which when used in place of an alkylating catalyst in Example 1 in alkylating aromatic amines, will yield alkylated products in yields of 10 weight percent or less after 24 hours of reaction time. The amount of non-catalyst solid used is the same weight percent as the aluminum chloride catalyst in Example 1.

In FIG. 1, diphenylamine is alkylated with 2.7 molar equivalents of nonene using only $AlCl_3$ and with $AlCl_3$/non-catalyst solid system. The non-catalyst solid is silica. The weights of diphenylamine to aluminum chloride was roughly 10:1.04 and for diphenylamine, aluminum chloride, non-catalyst solid silica the weight ratios were roughly 10:1.04:1. Aliquots of the reaction were removed at given times and analyzed by NMR as outlined earlier. The compound being measured against time is the dialkyl diphenylamine. As is apparent from FIG. 1, the rate of formation of dialkylated product is faster for the aluminum chloride/solid system than for the aluminum chloride alone. It is also apparent that the yield of dialkylated product is greater for the catalyst system of this invention as opposed to using aluminum chloride alone. We have found that when silica was used as an alkylating catalyst in Example 1, little alkylation occurred even after 24 hours. Silica thus meets the definition of a non-catalyst solid for inclusion with an alkylating catalyst as described in this invention.

We have found that when the amount of aluminum chloride in the alkylating reaction was doubled so that the weight of aluminum chloride equaled the weight of aluminum chloride plus non-catalyst solid, the reaction closely followed that shown in FIG. 1 for using the catalyst system of this invention. This result is shown in FIG. 1.

Figure 2:
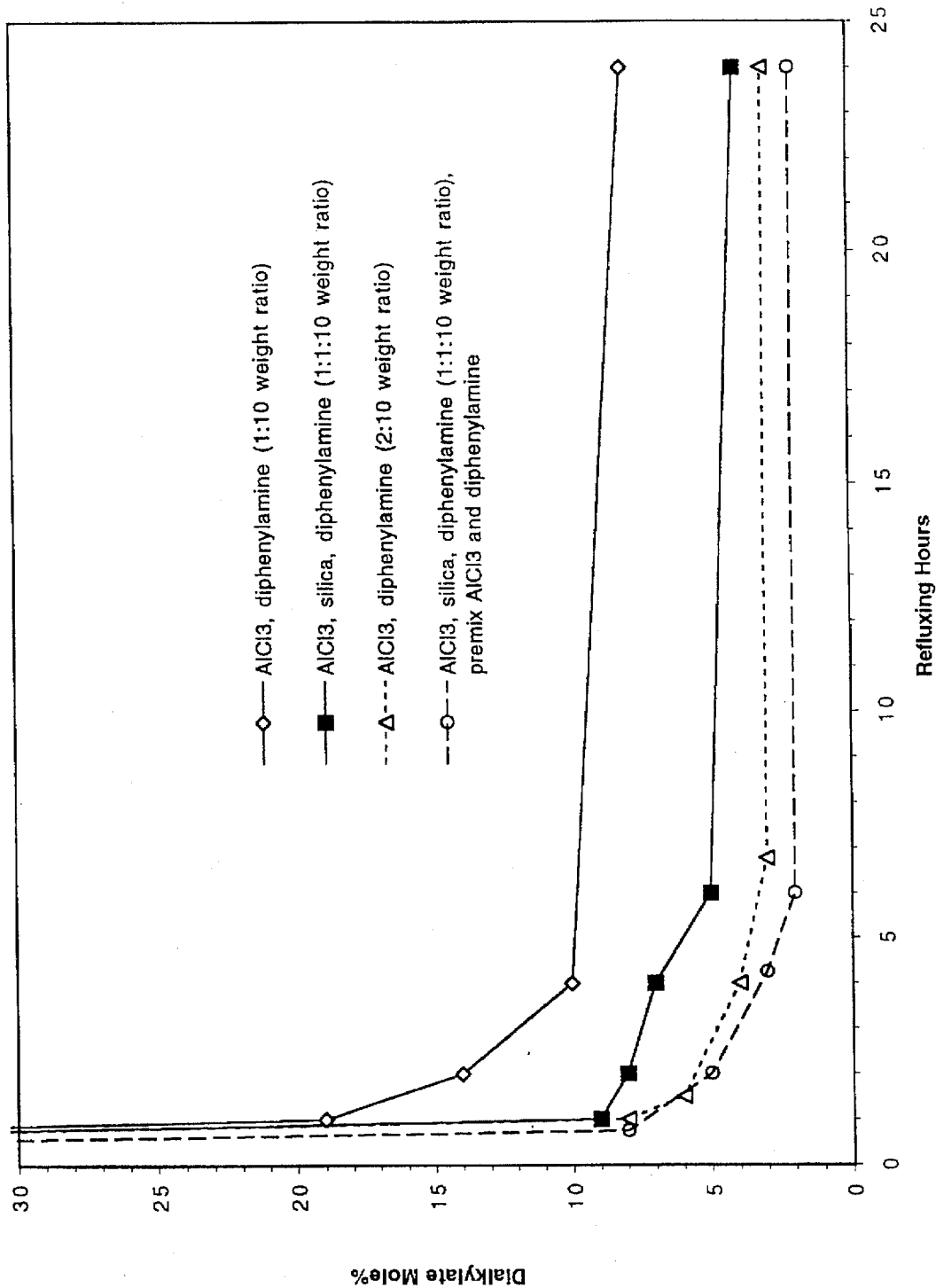

FIG. 2 shows the disappearance of diphenylamine with time during the alkylating reaction carried out as in FIG. 1. The rate of disappearance of diphenylamine is greater for the alkylation reaction using the catalyst system of this invention than using aluminum chloride alone when aluminum chloride is used at the same weight percent as in said catalyst system of this invention. Also, the residual diphenylamine in the reaction product is less for the catalyst system of this invention than aluminum chloride alone when aluminum chloride is used at the same weight percent as in said catalyst system of this invention.

It is apparent from the results shown in FIGS. 1 and 2 that the combined effect of the alkylating catalyst and non-catalytic solid is to form a catalyst system wherein the elements of the system are synergistic. This type of catalytic result has heretofore not been observed. The silica used in this invention showed little difference in its synergistic effects in combination with aluminum chloride. Silica in microspherical form, size: 0.09 mm; surface area: 330 $m^2$/gm; $N_2$ pore volume: 1.7 mL/g from PQ Corp. and silica gel 60, particle size <0.063 mm; <230 mesh from Fluka were used without significant difference when co-used with aluminum chloride.

When silica was reduced from a ratio of approximately 1:1 for aluminum chloride/silica, it was found that lower catalytic behavior resulted, but the catalytic alkylation effects were still greater than using aluminum chloride catalyst alone. For environmental and economic purposes, it is important that the silica used with the alkylating catalyst be recovered. It has been found that the reactivity of recovered silica is reduced but still useable in the catalyst system of this invention.

Alkylating catalysts useful in this invention may be used alone or in admixture to alkylate aromatic amines. Alkylating catalysts are selected from compounds containing Al, B, Ti, Sb, Sn, Fe, Cu and zinc or reactive equivalents thereof. A partial list includes the Friedel-Crafts Lewis acid catalysts including most commonly $AlCl_3$, $AlBr_3$, $TiCl_4$, $SnCl_4$, $SbCl_5$, $SbCl_3$, $FeCl_3$, $BF_3$, $ZnCl_2$ and $CuCl_2$. Super Lewis acids such as $SbF_5$, $NbF_5$, $AsF_5$ and $TaF_5$ as well as Bronsted-Lewis super acids may be used as alkylating catalysts. The latter are conjugated Friedel-Crafts' acids such as HCl-$AlCl_3$. A more complete list can be found in any text which includes Friedel Crafts' catalyst. What is important is that the catalyst will cause alkylation in high yield of an aromatic amine. The requirement of the non-catalyst solid is that it is capable only of minor catalytic activity in alkylation of aromatic amines. Such a solid as defined herein will cause less than 10 percent by weight conversion of diphenylamine to nonylated diphenylamine under conditions of Example 1 at 24 hour reaction time.

While we have found that silica and silica gel meet the definition of a non-catalyst solid, other materials may also be used. Such materials are non-activated, i.e. non-acid washed aluminas, silica-aluminas, filter aid, clays and the like. We have further found that some metal salts may be used as the non-catalyst solid part of the two component catalyst system of this invention. Such salts are, for instance, copper sulfate and calcium carbonate. In general, non-catalyst solids include salts of groups IA, IIA, VIII, IB, IIB or IVB metals. Mixtures of non-catalyst solids may also be used.

Alkylating agents useful in alkylating aromatic amines include alkylhalides, olefins, alcohols and epoxides and other types of compounds well-known to those skilled in the art. For forming alkylated aromatic amines for use in lubricants, low molecular weight olefins are the alkylating agents of choice.

FIGS. 1 and 2 also show the results of carrying out Example 2 with a different mixing sequence. In this, diphenylamine and aluminum chloride heated to 120° C. with stirring in about one hour under nitrogen gas to form a liquid. The mixture was cooled to about 95° C. and the silica added and the mixture stirred and heated to 150° C. and nonene was added. The mixture was then heated with stirring for up to 24 hours. Aliquots of this reaction were taken at various times and analyzed by the NMR method. The results are shown in FIGS. 1 and 2. By using this reaction sequence, it is demonstrated that the yield of dialkylated diphenylamine is slightly higher and the residual diphenylamine slightly lower than the improved alkylation reaction of Example 2.

What is claimed is:

1. A method for alkylating aromatic amines, said method comprising the steps of:
   (1) forming an alkylating mixture comprising:
      (a) an aromatic amine;
      (b) an alkylating agent;
      (c) a catalyst system comprising an aromatic amine alkylating catalyst and a non-catalyst solid;
   (2) heating said alkylating mixture for a given time at a given temperature to effect alkylation of said aromatic amine to form a reaction mixture comprising mono and dialkylated aromatic amines;
wherein the yield of alkylated aromatic amines is greater for said catalyst system than for said alkylating catalyst alone when said alkylating catalyst alone is used at the same weight percent as in said catalyst system under the same reaction conditions.

2. A method according to claim 1, wherein said aromatic amine alkylating catalysts are selected from the group consisting of Lewis acids, Friedel-Crafts, super Lewis acids and Bronsted Lewis acids and mixtures thereof.

3. A method according to claim 1, wherein said non-catalyst solids are catalysts supports such as silica, alumina, silica aluminas, clays, carbon and titania and mixtures thereof.

4. A method of claim 2, wherein said aromatic amine alkylating catalysts are selected from the group consisting of compounds containing Al, B, Ti, Sb, Sn, Fe, Cu, Zn, and reactive equivalents thereof, and mixtures thereof.

5. A method according to claim 4, wherein said catalysts are selected from the group consisting of $AlCl_3$, $AlBr_3$, $BF_3$, $TiCl_4$, $SbCl_5$, $SbCl_3$, $SnCl_4$, $FeCl_3$, $CuCl_2$, $ZnCl_2$, $SbF_5$, $N_6F_5$, $AsF_5$, and $TaF_5$ and reaction equivalents thereof or mixtures thereof.

6. A method according to claim 1, wherein said non-catalyst solids are salts selected from the groups consisting of Group IA, IIA, VIII, IB, IIB or IVB metals or mixtures thereof.

7. A method according to claim 6, wherein said metal salts are $CaCO_3$ and $CuSO_4$.

8. A method according to claim 1, wherein said catalyst system comprises aluminum chloride and silica.

9. A method according to claim 1, wherein said alkylating agent is an olefin, alkanol, alkyl halide, or an epoxide.

10. A method according to claim 1 wherein said aromatic amine is diphenylamine.

11. A method for alkylating diphenylamines, said method comprising the steps of:

(1) forming an alkylating mixture comprising:

(a) a diphenylamine;
(b) an olefin alkylating agent;
(c) a catalyst system mixture comprising aluminum chloride and silica;

(2) heating said mixture for a given time at a given temperature to effect alkylation of diphenylamine to form a reaction mixture comprising mono and dialkylated diphenylamine, wherein the yield of alkylated diphenylamines formation is greater for said catalyst system than for aluminum chloride alone when aluminum chloride is used at the same weight percent as in said catalyst system under the same reaction conditions.

12. The method according to claim 1, wherein in the measurable rate of formation of said alkylated aromatic amines is greater for said catalyst system than for the same alkylating catalyst alone when said catalyst alone is used at the same weight percent as in said catalyst system under the same reaction conditions.

13. The method according to claim 11, wherein the measurable rate of formation of alkylated diphenylamines is greater for said catalyst system than for aluminum chloride alone when aluminum chloride is used at the same weight percent as in said catalyst system under the same reaction conditions.

14. The method according to claim 1 or 11, wherein said alkylating agent is nonene.

\* \* \* \* \*